United States Patent [19]

Jones

[11] Patent Number: 5,286,632
[45] Date of Patent: Feb. 15, 1994

[54] METHOD FOR IN VIVO RECOMBINATION AND MUTAGENESIS

[76] Inventor: Douglas H. Jones, 2047 Aber Ave., Iowa City, Iowa 52246

[21] Appl. No.: 638,512

[22] Filed: Jan. 9, 1991

[51] Int. Cl.$^5$ .................. C12N 15/10; C12N 15/00; C12P 19/34
[52] U.S. Cl. .................. 435/91.2; 435/172.3
[58] Field of Search .................. 435/91, 172.3

[56] References Cited

PUBLICATIONS

Thomas et al. (1987), Cell 51: 503–512.
White et al. (1989), Trends in Genetics, vol. 5, No. 6, pp. 185–189.
Douglas H. Jones and Bruce H. Howard, National Cancer Institute, NIH, Biotechniques, "A Rapid Method for Site-Specific Mutagenesis and Directional Subcloning by Using the Polymerase Chain Reaction to Generate Recombinant Circles", vol. 8, No. 2 (1990), pp. 178–183.
K. Mullis, F. Faloona, S. Scharf, R. Saiki, G. Horn, and H. Erlich, Cetus Corporation Dept. of Human Genetics, Cold Spring Harbor Symposia on Quantitative Biology, vol. LI, pp. 263–273 (1986).
Randall K. Saiki, Stephen Scharf, Fred Faloona, Kary B. Mullis, Glenn T. Horn, Henry A. Erlich, Norman Arnheim, Science, "Enzymatic Amplification of β–Globin Genomic Sequences and Restriction Site Analysis for Diagnosis of Sickle Cell Anemia," vol. 230, pp. 1350–1354, Dec. 20, 1985.
Fandall K. Saiki, David H. Gelfand, Susanne Stoffel, Stephen J. Scharf, Russell Higuchi, Glenn T. Horn, Kary B. Mullis, Henry A. Erlich, Science, "Primer-Directed Enzymatic Amplification of DNA with a Thermostable DNA Polymerase," vol. 239, Jan. 29, 1988, pp. 487–491.
Wing L. Sung, Diana M. Zahab, Cathy A. MacDonald and Cherk S. Tam, "Synthesis of mutant parathyroid hormone genes via site-specific recombination directed by crossover linkers", Gene, 47 (1986) 261–267.
Wing L. Sung and Diana M. Zahab, "Site-Specific Recombination Directed by Single Stranded Crossover Linkers: Specific Deletion of the Amino-Terminal Region of the β-Galactosidase Gene in pUC Plasmids", DNA, vol. 6, No. 4, 1987 pp. 373–379.
Russell Higuchi, Barbara Krummel and Randall K. Saiki, "A general method of in vitro preparation and specific mutagenesis of DNA fragments: study of protein and DNA interactions," Nucleic Acids Research, Jul. 8, 1988, vol. 16, No. 15, pp. 7351–7367.
Robert M. Horton, Henry D. Hunt, Steffan N. Ho, Jeffrey K. Pullen and Larry R. Pease, "Engineering hybrid genes without the use of restriction enzymes: gene splicing by overlap extension," Gene, 77 (1989) pp. 61–68.
Steffan Ho, Henry D. Hunt, Robert M. Horton, Jeffrey K. Pullen and Larry R. Pease, "Site-directed mutagenesis by overlap extension using the polymerase chain reaction",: Gene, 77 (1989) 51–59.
Francois Vallette, Emmanuelle Mege, Allison Reiss and Milton Adesnik, "Construction of mutant and chimeric genes using the polymerase chain reaction," Nucleic Acids Research, vol. 17 No. 2 1989 pp. 723–733.

(List continued on next page.)

Primary Examiner—Richard A. Schwartz
Assistant Examiner—Philip W. Carter
Attorney, Agent, or Firm—Cheryl Becker

[57] ABSTRACT

The subject invention relates to a method referred to as recombination PCR (RPCR). In the method, the polymerase chain reaction is utilized to add double-stranded homologous ends to DNA. These homologous ends undergo recombination in vivo following transfection of host cells. The placement of these homologous ends, by the amplifying primers permits the rapid cloning of the desired mutant or recombinant, with a minimal number of steps and primers.

8 Claims, 4 Drawing Sheets

PUBLICATIONS

Hiroko Kadowaki, Takashi Kadowski, Fredric E. Wondisford and Simeon I. Taylor, "Use of polymerase chain reaction catalyzed by Taq DNA polymerase for site-specific mutagenesis," *Gene* 76 (1989) pp. 161–166.

Jeff Yon and Mike Fried, "Precise gene fusion by PCR," *Nucleic Acids Research*, vol. 17, No. 12 1989, p. 4895.

Matthias Kammann, Jurgen Laufs, Jeff Schell and Bruno Gronenborn, "Rapid insertional mutagenesis of DNA by polymerase chain reaction (PCR)", *Nucleic Acids Research*, vol. 17, p. 5404.

Richard M. Nelson and George L. Long, "A General Method of Site-Specific Mutagenesis Using a Modification of the *Thermus aquaticus* Polymerase Chain Reaction", *Analytical Biochemistry* 180, 1989 pp. 147–151.

Ann Hemsley, Norman Arnheim, Michael Dennis Toney, Gino Cortopassi and David J. Galas, "A simple method for site-directed mutagenesis using the polymerase chain reaction," *Nucleic Acids Research*, vol. 17, No. 16 1989 pp. 6545–6550.

Jones, D., K. Sakamoto, R. L. Vorce and B. H. Howard, "DNA mutagenesis and recombination," *Nature*, vol. 344, pp. 793–794 Apr. 1990.

METHOD FOR IN VIVO RECOMBINATION AND MUTAGENESIS

BACKGROUND OF THE INVENTION

1. Technical Field

The subject invention relates to a method in which the polymerase chain reaction is used to add homologous ends to DNA. These homologous ends undergo recombination in vivo following transfection of *E. coli* with linear PCR products. Therefore, the placement of homologous ends by PCR permits the formation of DNA joints in vivo. If the recombinant construct contains plasmid sequences that permit replication and a selectable phenotype, *E. coli* can be transformed with the construct of interest. Thus, the method can be used for the rapid generation of recombinant DNA constructs and for the generation of site-specific mutants.

2. Background Information

Two underpinnings of the recombinant DNA revolution are the capacity to recombine DNA, and the capacity to mutate a specific site in a DNA segment. Recently, the polymerase chain reaction (PCR) has gained use as a rapid means for the site-specific mutagenesis of DNA and for the recombination of DNA.

The polymerase chain reaction (PCR) is a method by which a specific DNA sequence can be amplified in vitro (U.S. Pat. Nos. 4,683,202, 4,683,195, Mullis et al., *Cold Spring Harbor Symposia on Quantitative Biology*, Vol. LI: 263–73 (1986), Saiki et al., *Science* 230:1350–54 (1985)). Prior investigators have used PCR to generate site-specific mutants (Hemsley et al., *Nucleic Acids Res.* 17:6545–51 (1989), Higuchi et al., *Nucleic Acids Res.* 16:7535–67 (1988), Ho et al., *Gene* 77:51–59 (1989), Kadowaki, *Gene* 76:161–66 (1989), Kammann et al., *Nucleic Acids Res.* 17:5404 (1989), Nelson et al., *Anal. Biochem.* 180:147–51 (1989) and Vallette et al., *Nucleic Acids Res.* 17:723–33 (1989)). PCR has also been used to amplify inserts which later undergo a separate subcloning procedure (Saiki et al., *Science* 239:487–91 (1988)).

Site-specific mutants are created by introducing mismatches into the oligonucleotides used to prime the PCR amplification. These oligonucleotides, with their mutant sequence, are incorporated into the PCR product. PCR has also been used to join segments of DNA by a method called splicing by overlap extension (Higuchi et al., *Nucleic Acids Res.* 16:7351–67 (1988), Ho et al., *Gene* 77:51–59 (1989), Horton et al., *Gene* 77:61–68 (1989)). This requires two sequential PCR amplifications, and is not designed to generate cohesive ends. Therefore, cloning of the product requires additional in vitro enzymatic manipulations following the PCR amplification.

A recent report describes a method for site-specific mutagenesis based on amplification of the entire plasmid (Hemsley et al., *Nucleic Acids Res.* 17:6545–51 (1989)). In that protocol, the ends of the PCR product are treated with the Klenow fragment of DNA polymerase 1. Subsequently, these ends are phosphorylated at the 5' terminus with Polynucleotide Kinase prior to an in vitro self-annealing blunt end ligation reaction.

The present inventor recently discovered a method for site-specific mutagenesis and for DNA recombination that requires no enzymatic reaction in vitro apart from DNA amplification (U.S. application Ser. No. 07/432,993 (filed on Nov. 8, 1989), Jones et al., *BioTechniques*, 8:178–83 (1990) and Jones et al., *Nature* 344:793–94 (April 1990)). This is accomplished by using separate PCR amplifications to generate products that when combined, denatured and reannealed form double-stranded DNA with discrete cohesive single-stranded ends that are complementary to each other and anneal to form DNA circles suitable for transformation of *E. coli*. This approach is termed recombinant circle PCR (RCPCR).

Others have used the ability of *E. coli* to recombine short stretches of homology to generate site-specific mutants in a method called the crossover linker technique. The crossover linker technique generates homologous ends, and the mutation of interest, by ligating a synthetic linker to a restriction enzyme digested plasmid (Sung et al., *Gene* 47:261–67 (1986) and Sung et al., *DNA*, 6:373–79 (1987)). This method can readily be distinguished from that of the subject invention.

All U.S. patents and publications referred to herein are hereby incorporated by reference.

SUMMARY OF THE INVENTION

The subject invention relates to a method referred to as recombination PCR (RPCR). In the method, the polymerase chain reaction is used to add double-stranded homologous ends to DNA. These homologous ends undergo recombination in vivo, following transfection of host cells, for example, *E. coli* cells. Therefore, the placement of homologous ends on PCR products permits the formation of DNA joints in vivo. This obviates the need to form staggered ends in vitro, reducing the number of primers necessary to generate a given mutant or recombinant, and bypassing the denaturation step in the RCPCR method discussed in copending application Ser. No. 07/432,993. The placement of these homologous ends, by the amplifying primers, permits the very rapid cloning of the desired mutant or recombinant with a minimal number of steps and primers.

In particular, the present invention relates to a method for synthesizing a double-stranded DNA molecule, using the polymerase chain reaction (PCR) process, comprising the steps of:

(i) amplifying a double-stranded DNA segment by means of PCR, wherein two primers effect said amplification and add nucleotide sequences to said segment, several of which are homologous to the ends of a second, double-stranded DNA segment;

(ii) transfecting said resulting product of step (i) into a host cell comprising said second, double-stranded DNA segment; and (iii) allowing the added nucleotide sequences of the product of step (i), which are homologous to the ends of said second double-stranded DNA segment, to recombine therewith, thereby producing a double-stranded DNA molecule. In this method, 3 basepairs of each of the nucleotide sequences which are added to said double-stranded DNA segment are homologous to at least one end of said second double-stranded DNA segment. The primers of step (i) are 10 nucleotides or more in length. The second, double-stranded DNA segment is co-transfected into the host cell, is part of the genome of the host cell or is extra-chromosomal DNA present in the host cell. The double-stranded DNA molecule may be, for example, circular.

The present invention also relates to a method of producing one or more site-specific mutations in a double-stranded circular DNA molecule comprising the steps of:

in a first container means containing a first aliquot of said double-stranded DNA molecule
  (i) contacting said double-stranded circular DNA molecule with a first and second primer wherein said first primer contains at least 10 nucleotides that are complementary to strand 1 of said double-stranded DNA, and said second primer contains at least 10 nucleotides that are homologous to said strand;
  (ii) producing non-circular copies of a portion of said double-stranded circular DNA molecule by means of the polymerase chain reaction;
in a second container means containing a second aliquot of said double-stranded circular DNA molecule:
  (iii) contacting said double-stranded circular DNA molecule with a third and fourth primer wherein said third primer contains at least 10 nucleotides that are complementary to strand 2 of said double-stranded circular DNA molecule and said third primer contains at least three nucleotides that are complementary to said first primer, and said fourth primer contains at least 10 nucleotides that are homologous to a portion of said strand 2 of said double-stranded circular DNA, and said fourth primer contains at least 3 nucleotides that are complementary to said second primer;
  (iv) producing non-circular copies of a portion of said double-stranded circular DNA molecule by means of the polymerase chain reaction using said third and fourth primers;
  (v) co-transfecting a host cell with the products of steps (ii) and (iv); and
  (vi) isolating said double-stranded circular DNA molecule containing at least one mutation, resulting from the co-transfection of step (v).

At least one of the four primers has sequence that is not present in the original template DNA, such that the recombinant molecule will contain an addition, deletion, or substitution of one or more nucleotides.

Furthermore, the invention also relates to a method of producing a site-specific mutation in a double-stranded circular DNA molecule comprising the steps of:
  (i) contacting said double-stranded circular DNA molecule with a first and second primer wherein said first primer contains at least 10 nucleotides that are complementary to one strand of said double-stranded DNA, said second primer contains at least 10 nucleotides that are homologous to said one strand, and said first primer contains at least 3 nucleotides that are complementary to said second primer;
  (ii) producing non-circular copies of a portion of said double-stranded circular DNA molecule by means of the polymerase chain reaction;
  (iii) transfecting a host cell with the product of step (ii);
  (iv) isolating said double-stranded circular DNA molecule, resulting from the transfection of step (iii).

At least one of the two primers has sequence that is not present in the original template DNA, such that the recombinant molecule will contain an addition, deletion, or substitution of one or more nucleotides.

Additionally, the invention includes a method of DNA recombination, with or without concurrent mutagenesis, resulting in the production of circular DNA, comprising the step of:

in a first container means containing an aliquot of double-stranded donor template DNA:
  (i) contacting said donor template DNA with a first and second primer wherein said first primer contains at least 10 nucleotides that are complementary to a portion of one strand of said double-stranded donor template DNA, and wherein said second primer contains at least 10 nucleotides that are homologous to a portion of said one strand of said donor template DNA;
  (ii) producing non-circular copies of a portion of said donor template DNA by means of the polymerase chain reaction;
in a second container means containing an aliquot of double-stranded recipient DNA:
  (iii) contacting said double-stranded recipient DNA with a third and fourth primer wherein said third primer contains at least 10 nucleotides that are complementary to a portion of one strand of said recipient DNA, and wherein said fourth primer contains at least 10 nucleotides that are homologous to a portion of said one strand of said recipient DNA,
  (iv) producing non-circular copies of a portion of said recipient DNA by means of the polymerase chain reaction using said third and fourth primers;
wherein said first primer contains at least three nucleotides that are complementary to a region of a first strand of the product of said third and fourth primers and said second primer contains at least three nucleotides that are complementary to a region of a second strand of the product of said third and fourth primers
or, alternatively, wherein said third primer contains at least three nucleotides that are complementary to a region of a first strand of the product of step (ii) and said fourth primer contains at least three nucleotides that are complementary to a region of a second strand of the product of step (ii),
  (v) co-transfecting a host cell with the product of steps (ii) and (iv); and
  (vi) isolating said circular DNA, resulting from the co-transfection of step (v). A restriction enzyme fragment may be substituted for the product of step (ii) or step (iv).

Moreover, the methods described above can also be utilized in kit form.

DETAILED DESCRIPTION OF THE INVENTION

The subject invention relates to a method in which homologous ends are added to plasmid sequences using PCR. The modified sequences are then used to transform host cells, for example, $E.$ $coli$ cells. Prior to transformation of the cells, the homologous ends undergo recombination. In this manner, site-specific mutants and DNA recombinant constructs may be generated easily as well as rapidly.

The present method (RPCR) is easier than the crossover linker technique, as it requires no enzymatic step beyond the PCR amplification. Moreover, since the homologous ends are generated using PCR, RPCR permits the placement of site-specific mutations without regard to restriction enzyme sites.

SITE-SPECIFIC MUTAGENESIS

Figure 1:
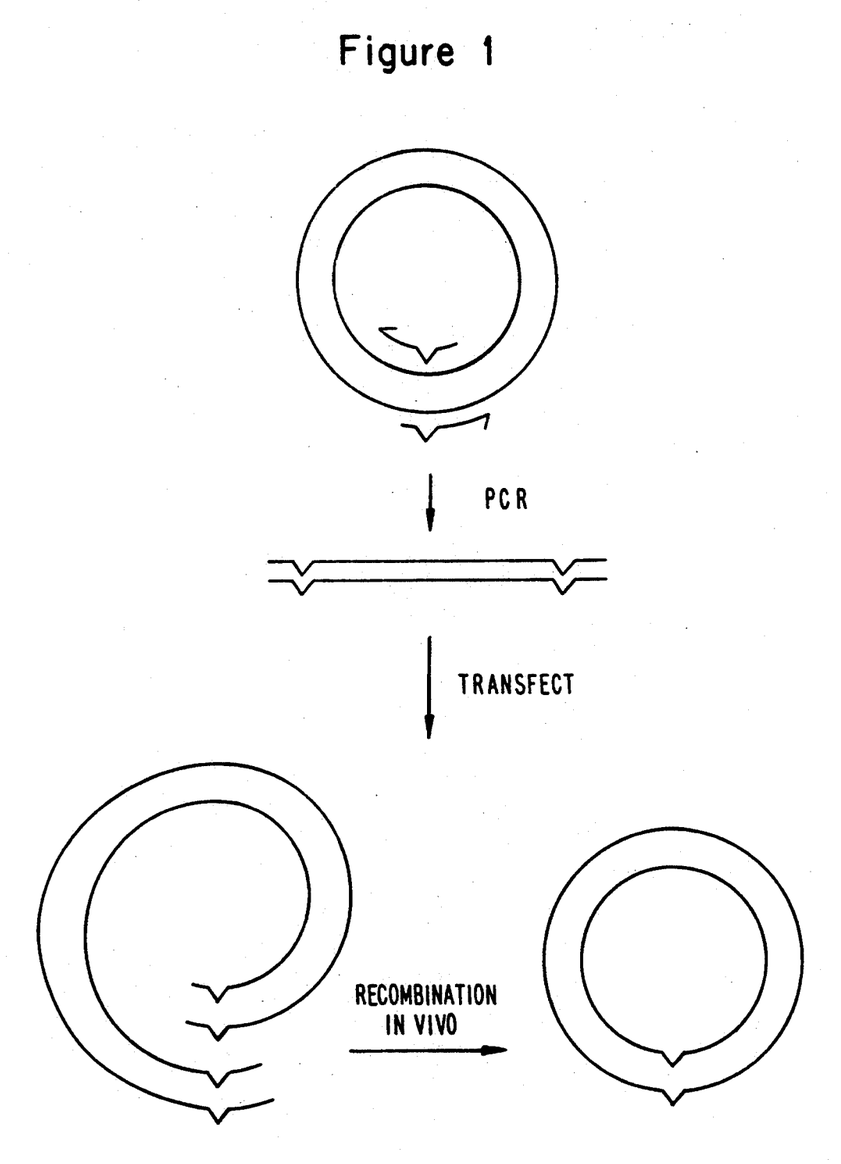
FIG. 1 illustrates the generation of a point mutation. The primers are hemiarrows. The 5' region of each primer is complementary to the other primer. Notches designate point mismatches in the primers and resulting mutations in the PCR products.

A basic strategy for site-specific mutagenesis using RPCR is illustrated in FIG. 1. The plasmid, containing the insert of interest, is simultaneously mutated and amplified using PCR. PCR is carried out in the usual manner. In addition to the site-specific mutation that is incorporated into the PCR product, the ends are modified so that they are homologous to each other. This is accomplished by using amplifying primers whose 5' ends are complementary to each other. More specifically, the primers are at least 10 basepairs long, and contain at least three nucleotides that are complementary to each other. Upon transfection of these linear products into $E.$ $coli$, those products that are circularized by recombination between these homologous ends will replicate. Use of a selectable phenotype, such as antibiotic resistance, causes the plasmids to persist. The ability to modify the ends of DNA molecules using PCR, and the propensity for $E.$ $coli$ to recombine these homologous DNA ends, can be used to generate DNA joints in vivo. Such joints may be used to join existing sequences, or to introduce deletions, insertions or substitutions.

Use of a selectable phenotype to isolate a plasmid from a host organism following transfection is a common practice in the art. Such a phenotype is frequently conferred by having an antibiotic resistance gene as part of the plasmid. If the bacteria are grown in the presence of the antibiotic, only those bacteria which have the plasmid expressing the antibiotic resistance gene will survive, and in this respect, the antibiotic resistance is a selectable phenotype, selecting for those bacteria that retain the plasmid. Use of a selectable phenotype allows one to isolate only those bacteria with the plasmid of interest, and select for the growth of only those bacteria that retain the plasmid. In this manner, large amounts of plasmid can be obtained.

In the site-specific mutagenesis application of the present method (FIG. 1), the mutagenesis site is contained in the overlapping sequence of each primer. The mutagenesis site can constitute a substitution, insertion or deletion. Note that the mutagenesis site need not be in both primers, and could be in the 3' region of only one primer that is outside the region of complementarity with the other primer, so long as priming could still be initiated (Sommer et al., $Nucleic$ $Acids$ $Res.$ 17:6749 (1989)). Furthermore, in an insertional mutagenesis protocol, the mutating sequence and the region of complementarity could be equivalent (Jones et al., $Nature$ 344:793-94 (1990)).

The method described above is superior to previous methods because it reduces the number of steps and primers necessary for the generation of site-specific mutants. More specifically, only two primers are necessary per site mutated, and no enzymatic step is required, in vitro, apart from PCR amplification. Furthermore, the isolated PCR product can be transfected directly into $E.$ $coli$ without any other manipulation, such as a separate denaturation and reannealing step.

DNA RECOMBINATION

Figure 2:
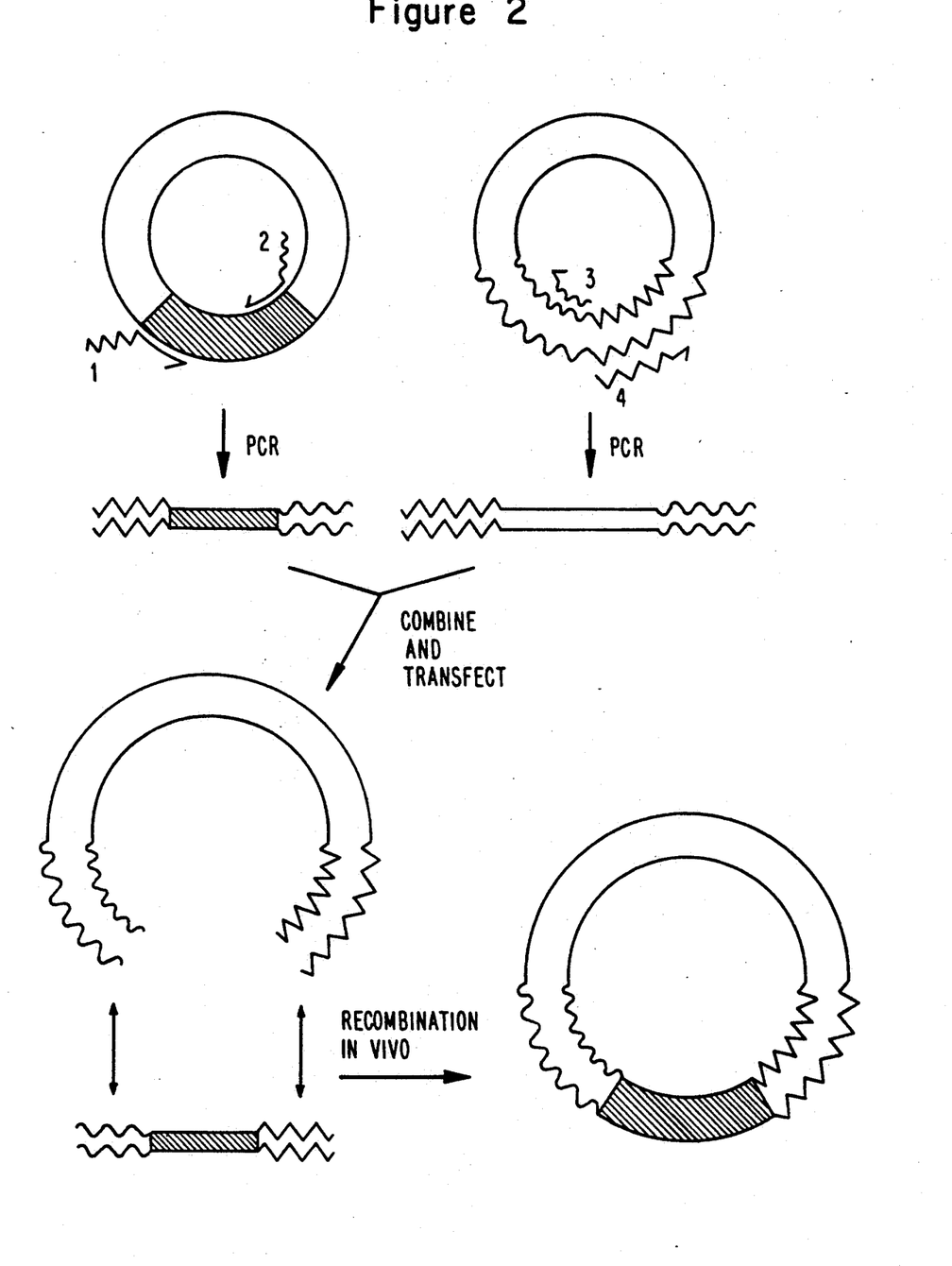
FIG. 2 illustrates the generation of a recombinant DNA construct. The primers are numbered hemiarrows. The insert is the cross-hatched region. Smooth circles represent the DNA strands of the donor plasmid. Circles with wavy and jagged portions represent DNA strands of the recipient plasmid.

RPCR is a particularly rapid method for the generation of recombinant DNA constructs. FIG. 2 illustrates a strategy for moving a segment of one plasmid into another plasmid at a specific location and with a defined orientation, using no enzymatic reaction apart from PCR, and using only 4 primers. The segment that is to be inserted into the recipient plasmid is amplified with primers 1 and 2. In a separate reaction, the recipient plasmid is amplified with primers 3 and 4. Primers 4 and 3 are complementary to the 5' regions of primers 1 and 2. Note that as long as the 5' regions of primers 1 and 2 are complementary to the 5' regions of primers 4 and 3 (or 3 and 4, depending on the orientation of the insert desired in the recombinant product), these four regions do not need to have homology to either the donor or recipient plasmid sequences. These overlapping regions may be used to join existing sequences or to introduce deletions, insertions or substitutions. Therefore, this strategy could be used for simultaneous mutagenesis of two distant regions in one construct (see FIG. 3), as an alternative for the rapid mutagenesis of single sites (see FIG. 4), or for concurrent mutagenesis and recombination of DNA. Following amplification, each PCR product is purified, and the two products are then transfected together directly into, for example, $E.$ $coli.$ There is a modification of the above protocol that facilitates the generation of DNA recombinants. If the two original template plasmids are cut by restriction enzymes outside the region to be amplified, no purification of PCR products is necessary because by eliminating supercoiled template, the frequency of background colonies containing an original template is greatly reduced. Furthermore, use of linearized templates greatly increases the amplification product yield, thereby diminishing the number of amplification cycles. Recombination occurs following co-transfection of the two crude PCR products.

Figure 3:
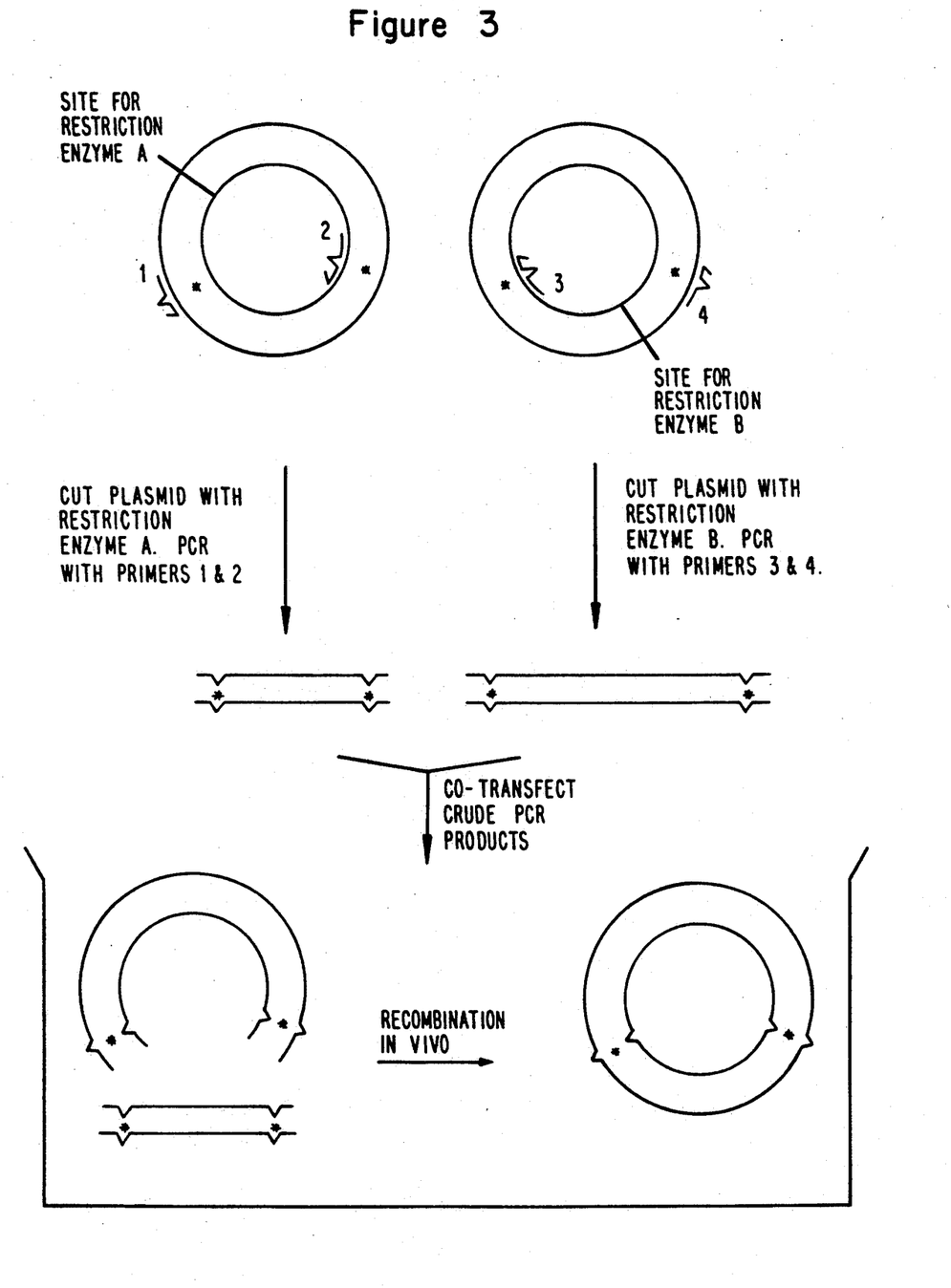
FIG. 3 illustrates the concurrent mutagenesis of two distant regions of DNA contained in a plasmid with no gel purification step. The primers are numbered hemiarrows. Asterisks designate the mutagenesis sites. Notches designate point mismatches in the primers and resulting mutations in the PCR products.
Figure 4:
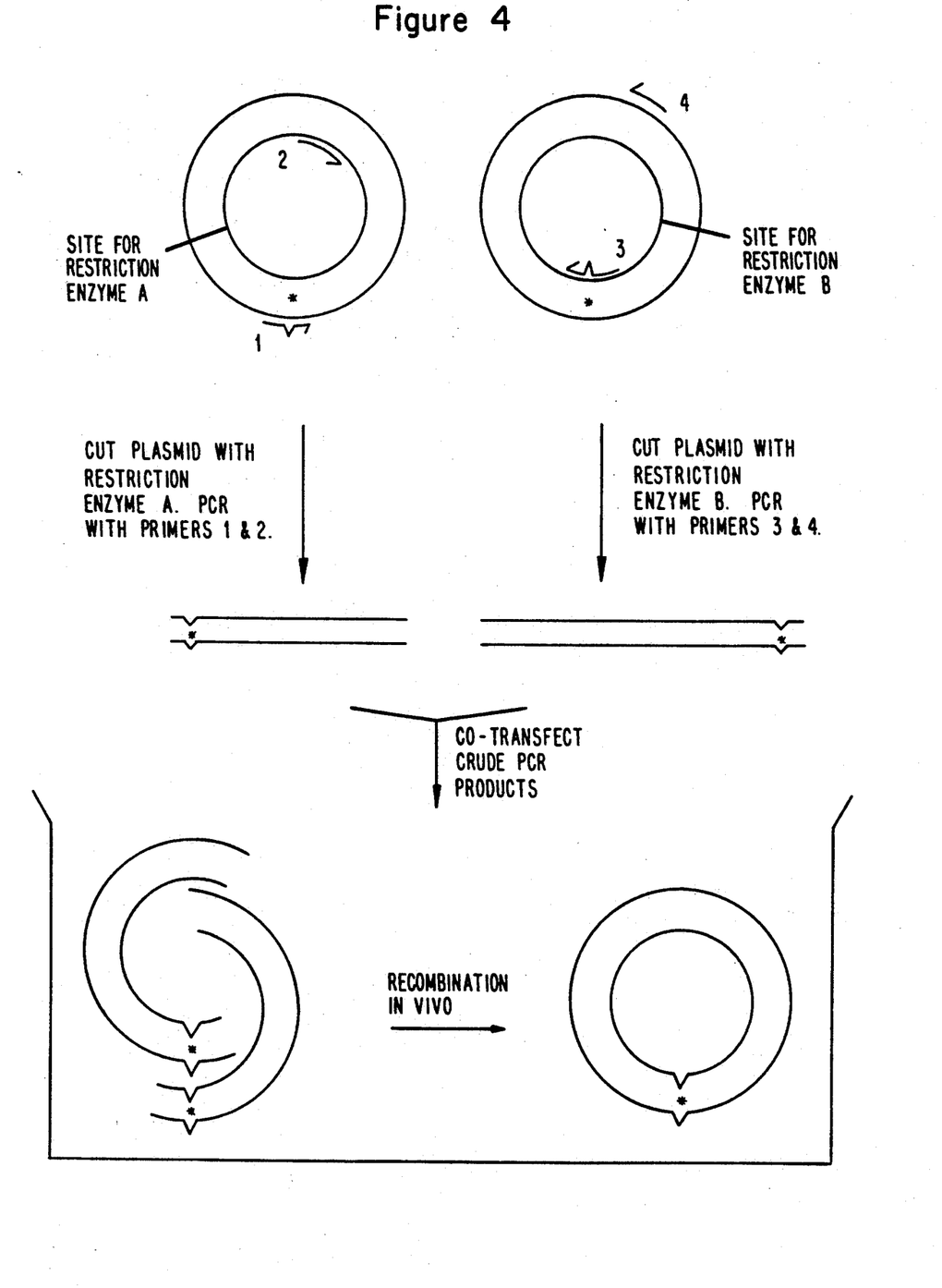
FIG. 4 illustrates the mutagenesis of one region of DNA contained in a plasmid, with no gel purification step. The primers are numbered hemiarrows. The asterisk designates the mutagenesis site. Primer 2 is complementary to primer 4. Restriction enzyme sites A and B bracket the insert. For each additional single site mutagenesis reaction, only a new primer 1 and primer 3 need to be synthesized, and the same cut templates can be used.

The application of RPCR to the simultaneous mutagenesis of two distal sites is accomplished by using the polymerase chain reaction in two separate amplifications to mutate the two sites and to add homologous ends to DNA (see FIG. 3). These homologous ends undergo recombination in vivo following transfection of $E.$ $coli$ with the linear PCR products. If the recombinant construct contains plasmid sequences that permit replication and a selectable phenotype, such as antibiotic resistance, E. coli can be transformed with the construct of interest. Linearization of the original circular plasmid template, outside the region to be amplified, permits transformation of E. coli with crude PCR products that have not undergone a gel purification step because the background colonies from the original supercoiled plasmid are largely eliminated. RPCR provides a very rapid means for the simultaneous mutagenesis of two distal sites. If two sites are to be mutated, and convenient restriction enzymes sites do not exist between these two sites on the insert, it would be possible to use this method for single-site mutagenesis by using primers 2 and 4 in FIG. 3 as non-mutating primers that bind to complementary regions of the vector. If rare restriction enzyme sites bracket the ends of the insert, as is the case with many plasmids, appropriate linearized templates could be generated for the mutagenesis of any single site in the insert (see FIG. 4). In this case, primers 2 and 4 would be nonmutating and would be conserved for each mutagenesis reaction, such that only two new primers would need to be generated for each mutagenesis reaction (primers 1 and 3). This would permit site-specific mutagenesis of many single sites in a very short period of time.

The primers must be at least 10 basepairs long and must contain at least 3 nucleotides of complementarity to a targeted region of DNA, and the polymerase chain reaction is carried out in the usual manner. The method described is superior to previous methods because it reduces the number of steps and primers necessary for the generation of recombinant constructs.

The present inventor recently introduced a method for the recombination and site-specific mutagenesis of DNA in double-stranded vectors by using PCR to generate circular products in vitro (Jones et al., *BioTechniques* 8:178-83 (1990) and Jones et al., *Nature* 344:793-94 (1990)). These circles, formed following the denaturation and reannealing of the PCR products, were transfected into E. coli and repaired in vivo.

The method of the present invention eliminates the need to form staggered ends in vitro. Therefore, RPCR decreases the number of primers necessary to generate a given site-specific mutant from 4 to 2, and the number of primers necessary to generate a recombinant construction from 8 to 4. In the past, amplification of products up to 6.1 kb has been successful using a supercoiled template. Since PCR amplification is more efficient using a linear template than a supercoiled template, it should be possible to amplify and mutate very large products using this method. RPCR bypasses the denaturation and re-annealing steps necessary with the earlier recombinant circle PCR method (RCPCR). RPCR simplifies the manipulation of DNA, and should become a method of choice for site-specific mutagenesis as well as for the generation of recombinant constructs. RPCR is particularly useful as a method for the rapid generation of recombinant constructs, and should also find widespread use for site-specific mutagenesis and for the generation of complex constructs requiring the simultaneous mutagenesis and recombination of DNA.

The primers of the present invention have all the physical attributes of primers in the ordinary polymerase chain reaction process. Thus, each primer comprises a sequence of at least about 10 nucleotides that is complementary to its intended template DNA. In this complementary sequence, the two nucleotides at the 3' end of the primer, where new DNA is to be added, are exactly complementary to their template, while one or more of the other nucleotides in the primer sequence that is complementary to its template may not be exactly complementary, provided the overall complementarity is sufficient to provide stable annealing of the primer to the template. This aspect of primer design is well known in the art. Such primers may be single-stranded oligonucleotides, single-stranded components of double-stranded oligonucleotides, single-stranded large fragments of DNA, or a single-strand of a large double-stranded fragment of DNA, such as a fragment generated following restriction enzyme digestion or a PCR product.

A region of homology between two sequences contains at least 3 nucleotides of identical sequence. A region of complementarity between two sequences contains at least 3 nucleotides of complementary sequence.

Basically, the present invention involves the use of PCR to add homologous ends to DNA in order to permit homologous recombination. In the examples given below, the homologous recombination takes place between PCR generated products in order to generate site-specific mutants or recombinant constructs. The generation of site-specific mutants and recombinant constructs could also take place by the homologous recombination between a product generated by PCR and another source of DNA. Such additional DNA could be the restriction enzyme product of a recipient vector. Homologous recombination by PCR modified DNA ends could also be used for the detection and amplification of specific sequences of DNA from a complex mixture. The two primers used in the amplification are at least 10 nucleotides long, and each contains at least 3 nucleotides that are complementary to a distinct targeted region in separate complementary strands of a segment or subset of segments in the complex mixture of DNA. The 3' ends of the two targeted regions in the complex mixture of DNA point toward each other. If the PCR modified DNA has sequences that permit replication and a selectable phenotype, transformation following homologous recombination by the PCR generated DNA could be used as a means for the specific amplification in vivo, of one sequence, or one family of sequences, from a complex mixture, and therefore could provide an alternative to PCR for the detection and amplification of specific sequences in a complex mixture. Furthermore, the homologous recombination by DNA ends modified through PCR could also be targeted to specific regions of the genome of prokaryotes or eukaryotes, providing a means for modifying specific sites in a genome. Therefore, the generation of DNA ends homologous to specific genomic sequences, by PCR, could be used for gene therapy.

It should also be noted that the above-described methods can be utilized in a kit format. More specifically, a portable self-contained kit can be developed for the generation of site-specific mutants. The kit may, for example, consist of the following: a) a plasmid in which mutagenesis is to occur, b) two primers for use in the amplification of the DNA of said plasmid, c) a fragment purification kit, d) competent bacteria, and e) additional primers which flank a polylinker region, wherein the 3' end of each primer is directed toward an inserted sequence, to be used for screening clones with PCR.

In addition, a portable self-contained kit can be developed for the generation of recombinant constructs, with or without concurrent mutagenesis. Such a kit can consist of the following: a) a recipient plasmid, b) a donor plasmid, c) a fragment purification kit, d) restriction enzymes which cut the recipient and/or donor plasmid outside the region to be amplified, e) the third and fourth primers (discussed above with respect to DNA recombination), f) competent bacteria, and g) additional primers which flank a region in the recipient plasmid wherein the 3' end of each primer is directed toward an inserted sequence, to be used for screening clones with PCR.

The present invention can be illustrated by the use of the following non-limiting examples.

EXAMPLE I

Site-Specific Mutagenesis

Initially, the use of RPCR was tested by eliminating, by point mutagenesis, the Pst I site in the lac Z' operon of pUC19. In particular, the Pst I site of pUC19 was eliminated using the following primers (mutation underlined, region of overlap in bold): tcaggcatgcaagcttggcgtaatcatggtcatagctgt and gattacgccaagcttgcatgcctgaaggtcgactctag see SEQ ID NOs:1 and 2, respectively). These two primers have 5' ends with 25 basepairs of overlapping (complementary) sequence, and 3' ends that extend 13 or 14 basepairs beyond the 25 basepair region of overlap (see FIG. 1).

Following 22 cycles of amplification, the PCR product was isolated by agarose gel electrophoresis, extracted with Geneclean (BIO101), La Jolla, Calif.), and suspended in TE. 1.5 ng of the recovered 45 ng was transfected into Max competent HB101 *E. coli* (BRL, Life Technologies, Gaithersburg, Md.), resulting in 400 colonies. 7 of 12 clones analyzed contained the mutation of interest. Sequencing of 350 nucleotides, with 150 bp surrounding each homologous region, revealed one error in 1 of the 7 clones (deletion of the A in base 462 (a primer sequence) of pUC19).

Use of control primers that anneal to nonoverlapping regions of the plasmid revealed that recombination, in the presence of minimal homology between DNA ends, can occur, but at a frequency approximately 200 fold lower/ng linear DNA. These regions of homology are short palindromes. In one of two sequenced clones, recombination occurred with only 4 bp of complementary sequence shared between each of the two primers (AGCT), with excision of the 5' ends of the PCR product. In the other clone, recombination occurred with only 2 bp of complementarity between an AT in one primer and an AT 4 bp downstream from the 3' end of the other primer, with excision of the ends of the PCR fragment.

The mechanism underlying this recombination between very short regions of homology is not known, but may share components with the RecE or RecF pathways (Stahl, F. W., *Progress in Nucleic Acid Res. Mol. Biol.* 33:169-94 (1986)).

1) Preparation and Purification of Plasmids

Plasmids for PCR or DNA sequencing were prepared by Triton X-100/lysozyme lysis and cesium chloride banding. (Davis et al., "Plasmid DNA Preparation Triton-Lysozyme Method," In Basic Methods in Molecular Biology, pp. 93-98 (1986)), or by Qiagen columns following the manufacturer's procedure (Qiagen Inc. Studio City, Calif.) Bluescript SKII+ was purchased from Stratagene (La Jolla, Calif.).

2) Oligonucleotide Synthesis

Oligonucleotide primers were prepared on an Applied Biosystems DNA synthesizer (Foster City, Calif.) in the trityl-on mode. They were purified on Applied Biosystems purification cartridges and were not 5' phosphorylated. Restriction enzymes were purchased from BRL, Life Technologies (Gaithersburg, Md.).

The twenty-two cycles of amplification were carried out as follows:

3) PCR Amplification

PCR amplification was performed with Taq polymerase using a Perkin-Elmer Cetus Thermal Cycler (Norwalk, Conn.). Amplifications were in Taq buffer (50 mM KCl, 10 mM Tris-Cl, pH 8.3 1.5 mM $MgCl_2$, 0.01% w/v gelatin) with 200 $\mu$M each dNTP, 25 pmol each primer, 2 ng template and 1.25 U. Taq polymerase (Perkin Elmer Cetus) in 50 $\mu$l. Reactants underwent initial denaturation (94° C.$\times$1 min), repetitive amplification cycles (94° C.$\times$30 s, 50° C.$\times$30 sec., and 72° C.$\times$1 min/kb PCR product) and a final extension (72° C.$\times$7 min.).

4) Purification of PCR Product

The entire PCR product was removed by inserting a long thin micropipette tip through the top mineral oil layer and drawing up the sample. The entire unpurified PCR product was mixed with 5 $\mu$l of 10$\times$electrophoresis loading buffer, and underwent electrophoresis through standard high melting point 1% agarose in TAE buffer with 0.5 $\mu$g/ml ethidium bromide. Electrophoresis was carried out until the PCR product travelled at least 4 cm, in order to adequately separate the PCR products from the supercoiled template. The PCR product was visualized with uv light, cut out with a razor blade, and removed using Geneclean. The PCR product was then suspended in 30 $\mu$l TE.

The *E. coli* cells were subsequently transformed and the colonies screened as follows:

5) Transformation of *E. coli*

1-5 $\mu$l of the PCR product was used to transform Max competent HB 101 *E. coli* (BRL, Life Technologies, Gaithersburg, Md.). The manufacturer's protocol was utilized with the following modifications: 1) Only 50 $\mu$l of *E. coli* were used for each sample transfected. 2) After incubation at 37° C. in a shaker for 1 hour, the sample was not diluted prior to plating; the entire sample was plated directly only an LB plate containing 100 $\mu$g/ml Ampicillin. In order to keep the sample on the plate, 2 ml of top auger, at 42° C., was added to each sample immediately prior to pouring it onto the plate.

6) Screening of Colonies

Individual colonies were placed in 2-3 ml of LB broth containing 100 $\mu$g/ml of Ampicillin and grown overnight at 37° C. The bacteria were screened using PCR by a modification of the procedure of W. Liang and J. P. Johnson (*Nucleic Acids Res.* 16:3579 (1988)). 50 $\mu$l of each sample was placed in a 1.5 ml eppendorf tube and placed in boiling water for 2 minutes. Following centrifugation at top speed in a microcentrifuge for 2 seconds, each eppendorf tube was placed on ice. 2 $\mu$l of the sample supernatant, without plasmid purification, underwent 25 cycles of PCR amplification using primers that flank the mutagenesis site or insert (i.e., AGGGTTTTCCCAGTCACGAC and CGGATAA- CAATTTCACACAGGA) (see SEQ ID NOs: 3 and 4, respectively).

Five μl of each PCR product was removed, and the colonies are screened by addition of the restriction enzyme Pst I and appropriate 10× restriction buffer directly to 5 μl of the unpurified PCR product in a total volume of 10 μl. Clones were screened by minigel analysis.

The DNA of the clones was then sequenced as follows:

7) DNA Sequencing

The supercoiled form of each clone to be sequenced was visualized by agarose gel electrophoresis prior to sequencing. Sequencing of plasmids was done by the dideoxy method (Sanger et al., *Proc. Natl. Acad. Sci. USA* 74:5463-67 (1977)). Sequenase was used for this purpose (United States Biochemical, Cleveland, Ohio), and the manufacturer's protocol was observed.

EXAMPLE II

DNA Recombination

The use of RPCR for DNA recombination was tested by moving a 707 bp insert containing the EBER genes from pUC19 to Bluescript SK II+ (Jones et al., *BioTechniques* 8:178-83 (1990)). The following primers amplified EBER (region of overlap with Bluescript in bold): gataagcttgatatcgaattcctgcagcccccct-tacatgttgtgggtgcaa (primer 1, see SEQ ID NO: 5) and ggcggccgctctagaactagtggatcccccccataaagcccagggt-gtaaa (primer 2, see SEQ ID NO: 6). The following primers amplified Bluescript: gggggatccactagttctagag (primer 3, see SEQ ID NO: 7) and gggctgcaggaatt-cgatatca (primer 4, see SEQ ID NO: 8). In the basic recombination protocol, in which the PCR templates were not linearized prior to PCR amplification, EBER underwent 18 amplification cycles and Bluescript underwent 25 amplification cycles. Product purification by agarose gel electrophoresis followed by Geneclean (BIO 101) resulted in 300 ng amplified insert and 250 ng amplified recipient plasmid. 16 ng amplified insert and 0.3 ng amplified recipient plasmid were co-transfected into Max competent HB101 *E. coli*, yielding 22 colonies. 6 of 12 clones tested contained the recombinant. Sequencing 379 bp, in each of 4 clones, including 50 bp surrounding each region of homology, revealed no errors.

In a second protocol, each template was linearized by restriction enzyme digestion prior to PCR amplification outside of the region to be amplified (donor plasmid: SspI, recipient plasmid: SmaI). 14 amplification cycles resulted in 500 ng of the amplified insert and 1 μg of the amplified recipient plasmid. The yield of DNA was estimated by gel band intensity after ethidum bromide staining of an aliquot of each sample. Co-transfection of 25 ng (in 2.5 μl) of amplified insert and 50 ng (in 2.5 μl) of amplified recipient plasmid, without prior purification, resulted in 50 colonies in Max competent HB101 and 70 colonies in Max competent DHT5α (BRL Life Technologies). 11 of 15 HB101 clones analyzed contained the recombinant. Sequencing 379 bases in each of 4 clones revealed one error in 1 clone (elimination of an A from a primer sequence; 3 of 4 clones had no detected errors). 11 of 12 DH5α clones analyzed contained the recombinant. Sequencing 379 bp in each of 4 clones revealed 2 errors in the insert of one clone, each outside of the primer sequences (T for C substitution; elimination of a G), and no errors in 3 clones. Transfection with the amplified insert or amplified recipient plasmid alone did not yield the recombinant construct. To summarize, in each experiment, at least 50% of the resulting clones analyzed contained the insert in the recipient plasmid without a detected error.

(See Example 1 for a discussion of amplification, transfection, sequencing as well as the steps utilized in such a procedure, for example, preparation and purification of the plasmids.)

EXAMPLE III

Site-Specific Mutagenesis of Two Distal Sites

Using the conditions described for DNA recombination the Ndel site and Pst1 sites of pUC19 were simultaneously mutated, by substituting a C for an A at nucleotide #186, and by substituting a T for the G at nucleotide #437.

In PCR #1, pUC19 was linearized by digestion with Sspl prior to amplification with the following primers (primer 1 (see SEQ ID NO: 9): acgccaagcttgcatgc-ctoaaggtcgactct, primer 2 (see SEQ ID NO: 10): tgtact-gagagtgcaccatctgcggtg; mutation underlined). In PCR #2, pUC19 was linearized by digestion with EcoRI prior to amplification with the following primers (primer 3 (see SEQ ID NO: 11): ggatcctctagagtcgacctt-caggcatgca, primer 4: gcggtatttcacaccgcagatggtggt-gcact mutation underlined; region of complementarity of primer 1 to primer 3, and region of complementarity of primer 2 to primer 4 (see SEQ ID NO: 12) in bold). The yield of DNA was estimated by gel band intensity after ethidium bromide staining. PCR #1 yielded 300 ng DNA and PCR #2 yielded 1 μg DNA. 15 ng of PCR #1 (in 2.5 μl) and 50 ng of PCR #2 (in 2.5 μl) were cotransfected into Max competent DH5α *E. coli*, resulting in 600 colonies.

Restriction enzyme screening of the plasmids in 12 of the resulting colonies revealed that both sites were mutated in all 12 clones. Sequence analysis of 475 bp in each of 6 of these clones (pUC19 nucleotides 137–611; total 2850 bp) confirmed mutagenesis in each of the two sites, and revealed no sequence errors. Therefore, 100% of the clones tested contained both mutations of interest, without detected errors.

(See Example 1 for a discussion of amplification, transfection, sequencing as well as the steps utilized in such a procedure, for example, preparation and purification of the plasmids.)

---

What is claimed is:

1. A method for synthesizing a double-stranded circular DNA molecule, using the polymerase chain reaction (PCR) process, comprising the steps of:
   (i) amplifying a double-stranded DNA segment by means of PCR, wherein two primers effect said amplification and add nucleotide sequences to said segment, several of which are homologous to the ends of a linear, second, double-stranded, extra-chromosomal DNA molecule;
   (ii) transfecting the resulting product of step (i) into a host cell comprising said linear, second, double-stranded, extra-chromosomal DNA molecule; and
   (iii) allowing the added nucleotide sequences of the product of step (i), which are homologous to the ends of said linear, second, double-stranded, extra-chromosomal DNA molecule, to recombine therewith, thereby producing a double-stranded circular DNA molecule.

2. The method of claim 1 wherein 3 basepairs of each of the nucleotide sequences which are added to said double-stranded DNA segment are homologous to at least one end of said linear, second, double-stranded, extrachromosomal DNA molecule.

3. The method of claim 1 wherein the primers of step (i) are 10 nucleotides or more in length.

4. The method of claim 1 wherein said linear, second, double-stranded, extrachromosomal DNA molecule is co-transfected into said host cell.

5. A method of producing one or more site-specific mutations in a double-stranded circular DNA molecule comprising the steps of:
   in a first container means containing a first aliquot of said double-stranded DNA molecule:
   (i) contacting said double-stranded circular DNA molecule with a first and second primer wherein said first primer contains at least 10 nucleotides that are complementary to strand 1 of said double-stranded DNA, and said second primer contains at least 10 nucleotides that are homologous to said strand;
   (ii) producing non-circular copies of a portion of said double-stranded circular DNA molecule by means of the polymerase chain reaction;
   in a second container means containing a second aliquot of said double-stranded circular DNA molecule:
   (iii) contacting said double-stranded circular DNA molecule with a third and fourth primer wherein said third primer contains at least 10 nucleotides that are complementary to strand 2 of said double-stranded circular DNA molecule and said third primer contains at least three nucleotides that are complementary to said first primer, fourth primer contains at least 10 nucleotides that are homologous to a portion of said strand 2 of said double-stranded circular DNA, and said fourth primer contains at least 3 nucleotides that are complementary to said second primer;
   (iv) producing non-circular copies of a portion of said double-stranded circular DNA molecule by means of the polymerase chain reaction using said third and fourth primers;
   (v) co-transfecting a host cell with the products of steps (ii) and (iv); and
   (vi) isolating said double-stranded circular DNA molecule containing at least one mutation, resulting from the co-transfection of step (v).

6. A method of producing a site-specific mutation in a double-stranded circular DNA molecule comprising the steps of:
   (i) contacting said double-stranded circular DNA molecule with a first and second primer wherein said first primer contains at least 10 nucleotides that are complementary to one strand of said double-stranded DNA, said second primer contains at least 10 nucleotides that are homologous to said one strand, and said first primer contains at least 3 nucleotides that are complementary to said second primer;
   (ii) producing non-circular copies of said double-stranded circular DNA molecule by means of the polymerase chain reaction;
   (iii) transfecting a host cell with the product of step (ii);
   (iv) isolating said double-stranded circular DNA molecule, resulting from the transfection of step (iii).

7. A method of DNA recombination, with or without concurrent mutagenesis, resulting in the production of circular DNA, comprising the steps of:
   in a first container means containing an aliquot of double-stranded donor template DNA:
   (i) contacting said donor template DNA with a first and second primer wherein said first primer contains at least 10 nucleotides that are complementary to a portion of one strand of said double-stranded donor template DNA, and wherein said second primer contains at least 10 nucleotides that are homologous to a portion of said one strand of said donor template DNA;
   (ii) producing non-circular copies of a portion of said donor template DNA by means of the polymerase chain reaction;
   in a second container means containing an aliquot of double-stranded recipient DNA:
   (iii) contacting said double-stranded recipient DNA with a third and fourth primer wherein said third primer contains at least 10 nucleotides that are complementary to a portion of one strand of said recipient DNA, and wherein said fourth primer contains at least 10 nucleotides that are homologous to a portion of said one strand of said recipient DNA, (iv) producing non-circular copies of a portion of said recipient DNA by means of the polymerase chain reaction using said third and fourth primers;

wherein said first primer contains at least three nucleotides that are complementary to a region of a first strand of the product of said third and fourth primers and said second primer contains at least three nucleotides that are complementary to a region of a second strand of the product of said third and fourth primers or, alternatively, wherein said third primer contains at least three nucleotides that are complementary to a region of a first strand of the product of step (ii) and said fourth primer contains at least three nucleotides that are complementary to a region of a second strand of the product of step (ii), (v) co-transfecting a host cell with the product of steps (ii) and (iv); and (vi) isolating said circular DNA, resulting from the co-transfection of step (v).

8. The method of claim 7 wherein a restriction enzyme fragment is substituted for the product of step (ii) or step (iv).

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

| | |
|---|---:|
| TCAGGCATGC AAGCTTGGCG TAATCATGGT CATAGCTGT | 39 |

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

| | |
|---|---:|
| GATTACGCCA AGCTTGCATG CCTGAAGGTC GACTCTAG | 38 |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

| | |
|---|---:|
| AGGGTTTTCC CAGTCACGAC | 20 |

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

| | |
|---|---:|
| CGGATAACAA TTTCACACAG GA | 22 |

( 2 ) INFORMATION FOR SEQ ID NO:5:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

| | |
|---|---:|
| GATAAGCTTG ATATCGAATT CCTGCAGCCC CCCTTACATG TTGTGGGTGC AA | 52 |

( 2 ) INFORMATION FOR SEQ ID NO:6:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:6:

GGCGGCCGCT CTAGAACTAG TGGATCCCCC CCATAAAGCC CAGGGTGTAA A    51

( 2 ) INFORMATION FOR SEQ ID NO:7:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:7:

GGGGGATCCA CTAGTTCTAG AG    22

( 2 ) INFORMATION FOR SEQ ID NO:8:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:8:

GGGCTGCAGG AATTCGATAT CA    22

( 2 ) INFORMATION FOR SEQ ID NO:9:

( i ) SEQUENCE CHARACTERISTICS:
          ( A ) LENGTH: 32 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:9:

ACGCCAAGCT TGCATGCCTG AAGGTCGACT CT    32

( 2 ) INFORMATION FOR SEQ ID NO:10:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:10:

TGTACTGAGA GTGCACCATC TGCGGTG    27

( 2 ) INFORMATION FOR SEQ ID NO:11:

( i ) SEQUENCE CHARACTERISTICS:
          ( A ) LENGTH: 31 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:11:

GGATCCTCTA GAGTCGACCT TCAGGCATGC A    31

( 2 ) INFORMATION FOR SEQ ID NO:12:

(i) SEQUENCE CHARACTERISTICS:
   (A) LENGTH: 29 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:12:

GCGGTATTTC ACACCGCAGA TGGTGCACT                              29